(12) United States Patent
Nagatsuka

(10) Patent No.: US 6,974,954 B2
(45) Date of Patent: Dec. 13, 2005

(54) RADIATION IMAGING APPARATUS AND RADIOGRAPHING METHOD FOR RADIATION IMAGING APPARATUS

(75) Inventor: Sumiya Nagatsuka, Hino (JP)

(73) Assignee: Konica Corporation, (JP)

(*) Notice: Subject to any disclaimer, the term of this patent is extended or adjusted under 35 U.S.C. 154(b) by 265 days.

(21) Appl. No.: 10/370,832

(22) Filed: Feb. 21, 2003

(65) Prior Publication Data

US 2003/0165215 A1  Sep. 4, 2003

(30) Foreign Application Priority Data

Feb. 28, 2002 (JP) .............................. 2002-054157

(51) Int. Cl.$^7$ .............................................. G01T 1/24
(52) U.S. Cl. .............................................. 250/370.09
(58) Field of Search ...................... 250/370.08, 370.09, 250/370.11

(56) References Cited

U.S. PATENT DOCUMENTS

| | | | |
|---|---|---|---|
| 5,263,004 A | 11/1993 | Larson, III | 367/7 |
| 5,446,292 A | 8/1995 | Kohda | 250/585 |
| 5,825,032 A * | 10/1998 | Nonaka et al. | 250/370.09 |
| 6,423,973 B2 * | 7/2002 | Choo et al. | 250/370.09 |

FOREIGN PATENT DOCUMENTS

| | | |
|---|---|---|
| JP | 60088936 | 5/1985 |
| WO | WO 93/14418 | 7/1993 |
| WO | WO 97/05658 | 2/1997 |

* cited by examiner

*Primary Examiner*—Constantine Hannaher
(74) *Attorney, Agent, or Firm*—Squire, Sanders & Dempsey L.L.P.

(57) ABSTRACT

A radiation imaging apparatus, including
a radiation or fluorescence detecting device on which a plurality of imaging elements are arranged in a form of a plane, having
a sensor element, arranged on the imaging element, to detect radiation or fluorescence converted from the radiation which have passed through a subject, and to form radiation intensity signals, and
a switching element, arranged on the imaging element, to perform switching of read-out of signals that show the intensity of radiation outputted from the sensor element; and
a correcting device for correcting the radiation intensity signals, based on an angle of incidence of the radiation to the sensor element.

1 Claim, 3 Drawing Sheets

RADIATION IMAGING APPARATUS AND RADIOGRAPHING METHOD FOR RADIATION IMAGING APPARATUS

BACKGROUND OF THE INVENTION

The present invention relates to a radiation imaging apparatus and a radiographing method for the radiation imaging apparatus.

Hitherto, radiation images, represented by X-ray images, are widely used for medical diagnosis, and X-ray imaging apparatus are known as apparatus for effecting the X-ray images.

The X-ray imaging apparatus generally use an X-ray film as an X-ray detector to detect the X-rays having penetrated a subject, but in recent years, a flat panel detector (hereinafter referred to as FPD) which can change detected X-rays to electrical signals has been proposed.

FPDs are commonly composed of an X-ray/fluorescence conversion layer that converts the X-rays to fluorescent light, a photoelectric conversion layer, located under the X-ray/fluorescence conversion layer, which detects the fluorescence that is converted by the X-ray/fluorescence conversion layer, and converts the fluorescence to electrical signals, and a glass base plate, located under the photoelectric conversion layer, of a predetermined thickness.

The X-ray/fluorescence conversion layer is the one in which fluorescent substance crystals used for a screen film (S/F), for example, are structured as a flat. The fluorescent substance has the nature to radiate the fluorescence proportional to the intensity of the X-rays that are radiated by the X-ray radiating apparatus which they penetrate the subject.

On the other hand, the photoelectric conversion layer is the one in which a number of imaging elements are arranged as a matrix, and is composed of light receiving sections such as light receiving sensors which detect the fluorescence converted from the X-rays, and switching sections such as TFTs (thin film transistors) which perform switching of the read-out performed by an electrical signal read-out device of the electrical signal outputted from the light receiving section.

Incidentally, the light receiving section and the switching section are formed from semiconductors such as amorphous silicone, and arranged adjacent to each other on the glass base plate. Further, the top of the light receiving section is a surface (hereinafter referred to as a light receiving surface) for receiving light.

Still further, there is another type of FPD that has not X-ray/fluorescence conversion layer, but has an X-ray/electrical signal conversion layer having an X-ray receiving section that directly converts the irradiated X-rays to electrical signals. Under the structure mentioned above, the top of the X-ray receiving section is the surface for receiving the X-rays (hereinafter referred to as an X-ray receiving surface), which has the same structure as the above-mentioned light receiving section.

Incidentally, electrical signals are read out by an electrical signal read-out device, and are converted to digital image data by an A/D converter, which are stored in a memory device (not illustrated).

Incidentally, when X-ray radiography is performed, it is necessary to perform a so-called slanting radiograph based on the radiographing region, that is, the radiating angle of the X-rays to the radiographing region is set to be slanted from a right angle.

However, for FPDs having an X-ray/fluorescence conversion layer, the height of the surface which receives light is less than that of the switching section, and accordingly, when the slanting radiography is effected, some of the light receiving surface is shaded by the switching section, and an amount of the light rays received by the light receiving surface becomes less.

Further, for FPDs having an X-ray/electrical signal conversion layer instead of the X-ray/fluorescence conversion layer, the height of the X-ray receiving surface is less than that of the switching section, and when the slanting radiography is effected, a part of the X-ray receiving surface is shaded by the switching section, and accordingly, the amount of the X-rays received by the X-ray receiving surface becomes less.

Due to this, the quality of the X-ray images formed by the slanting radiography is reduced.

SUMMARY OF THE INVENTION

It is an objective of the present invention to provide a radiation imaging apparatus which can produce a radiation image having high resolution and a radiography method for the slanting radiograph in the radiation imaging apparatus. The objective of the present invention can be attained by the following structures.

Structure (1)

In a radiation imaging apparatus using a flat panel detector on which a large number of imaging elements are arranged on a plane, having, a sensor element that detects radiation or detects fluorescence converted from the radiation, and a switching element that performs switching of reading-out signals that show the intensity of the radiation outputted from the sensor elements, the radiation imaging apparatus is characterized in that when radiography is effected at a slanted radiating angle of the radiation to the radiographing region, slanted from a right angle to the frontal surface of the flat panel detector, there is provided a correcting device that corrects signals showing the intensity of radiation outputted from the sensor element, based on the radiating angle of the radiation.

According to Structure (1), when radiography is effected at the slanted radiating angle of radiation to the radiographing region, that is slanted from a right angle to the front surface of the flat panel detector, provided is a correcting device that adjusts the signal showing the intensity of radiation outputted from the sensor element, based on the radiating angle, and thereby, it is possible to produce the radiation images at high resolution, because the signal showing the intensity of the radiation outputted from the sensor element can be adjusted based on the radiation angle, even though the amount of radiation received by the sensor element or the amount of fluorescence converted from the radiation, is decreased.

Structure (2)

In a radiation imaging apparatus using a flat panel detector on which a large number of imaging elements are arranged on a plane, having, a sensor element that detects radiation or fluorescence converted from the radiation, and a switching element that switches read-out signals that show intensity of the radiation outputted from the sensor element, the radiation imaging apparatus is characterized in that the flat panel detector is provided with reflecting plates which reflect at least part of the radiation, slanted to the flat panel detector, or at least part of the fluorescence converted from the radiation.

According to Structure (2), the flat panel detector is provided with reflecting plates which reflect at least part of the radiation at a slant to the flat panel detector, or at least part of the fluorescence converted from the radiation, and thereby, among the incident radiation or fluorescence converted from the radiation, the incident radiation or fluorescence converted from radiation, which cannot be detected directly by a sensor element due to an obstacle such as the switching element, can be reflected to the sensor element by the reflecting plate. Accordingly, there is no decrease of the amount of radiation or the amount of fluorescence, received by the sensor element, and thereby, deterioration of sensitivity caused by a slanting radiography is prevented, making it possible to obtain radiograph images having the high resolution.

Structure (3)

In a radiation imaging apparatus using a flat panel detector on which a large number of imaging elements are arranged on a plane, having, a sensor element that detects radiation or detects the fluorescence converted from the radiation, and a switching element that switches read-out signals that show intensity of the radiation outputted from the sensor element, the flat panel detector of the radiation imaging apparatus is characterized in that the height of the surface of the sensor elements, by which the radiation or the fluorescence is received, is nearly equal to or greater than that of the switching elements.

According to Structure (3), the height of the surface of the sensor element in the flat panel detector by which radiation or fluorescence is detected, is nearly equal to or greater than that of the switching elements, and thereby, for slanting radiography, it is possible to precisely detect an incident radiograph or fluorescence converted from the radiation by the sensor elements, without the obstacle caused by the switching element. Accordingly, there is no decrease of the amount of radiation, or the amount of fluorescence, received by the sensor, and deterioration of sensitivity caused by slanting radiography, is prevented so that it is possible to obtain radiograph images of high resolution.

Structure (4)

In a radiation imaging method using a flat panel detector on which a large number of imaging elements are arranged on a plane, having, a sensor element that detects radiation or detects fluorescence converted from the radiation, and a switching element that switches read-out signals that show intensity of the radiation outputted from the sensor elements, the radiation imaging method is characterized in that when radiography is effected at a slanted radiating angle of the radiation to the radiographing region, slanted from a right angle to the frontal surface of the flat panel detector, signals showing intensity of radiation outputted from the sensor elements are corrected, based on the radiating angle of the radiation.

Structure (4) makes it possible to obtain the same effects as that of Structure (1).

DETAILED DESCRIPTION OF THE PREFERRED EMBODIMENT

Figure 1:
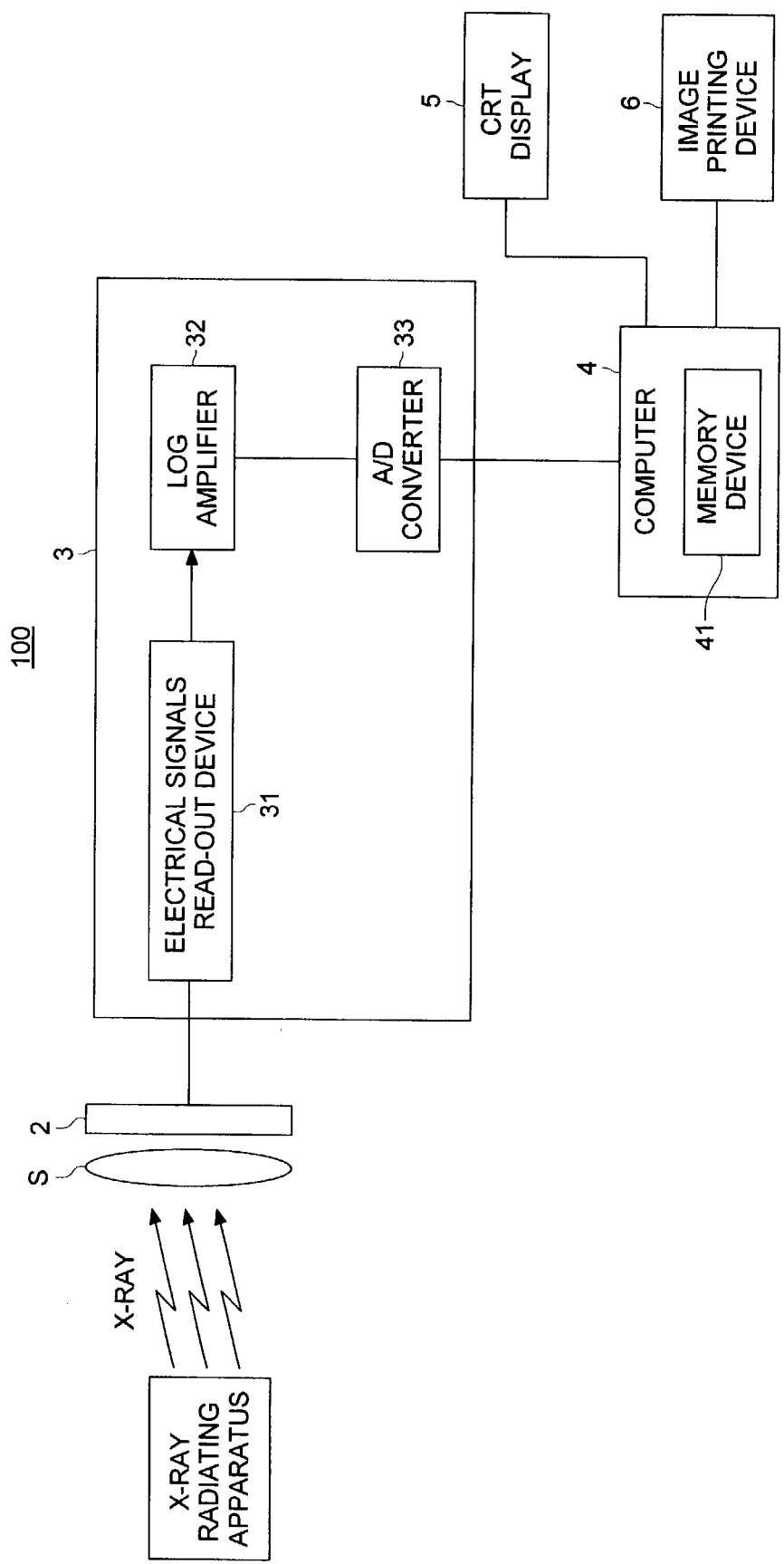
FIG. 1 is a block diagram of the main part of an X-ray imaging apparatus of an embodiment to which the present invention applies.

The preferred embodiment will be described in detail below, referring to the drawings. Incidentally, FIG. 1 is a block diagram of the main part of the X-ray imaging apparatus of the embodiment to which the present invention applies, FIG. 2(a) is a structural drawing showing the FPD arranged in the X-ray imaging apparatus in FIG. 1, and FIG. 2(b) is a cross-section illustrating the structure of the FPD including TFT in one imaging element.

As shown in FIG. 1, X-ray imaging apparatus (radiation image imaging apparatus) 100 shown in the present embodiment is provided with radiating apparatus 1 which radiates X-rays to subject S, flat panel detector (hereinafter referred to as FPD) 2 that converts the X-rays, which penetrate subject S, to electric signals (being signals that show the intensity of the radiation), digital conversion section 3 which reads out the converted electric signals and converts them to digital image data, computer 4 which controls storage of the digital image data, image processing, and outputting to the CRT display 5 (mentioned below), CRT which displays the X-ray image, and image printing device 6 which prints out the displayed X-ray image.

Figure 2A:
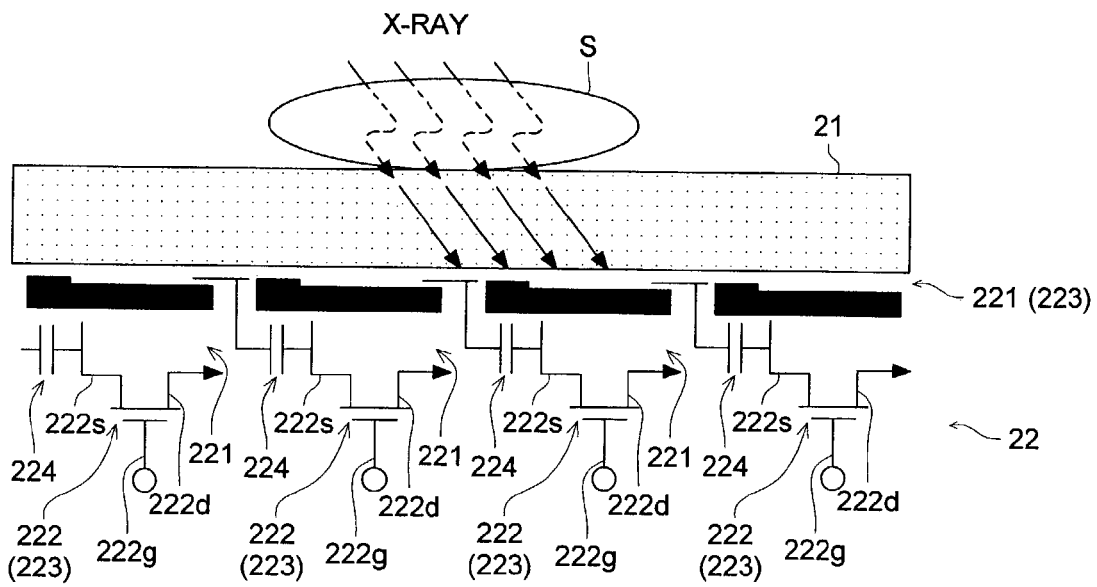
FIG. 2(a) is a structural drawing showing the FPD arranged in the X-ray imaging apparatus in FIG. 1.
Figure 2B:
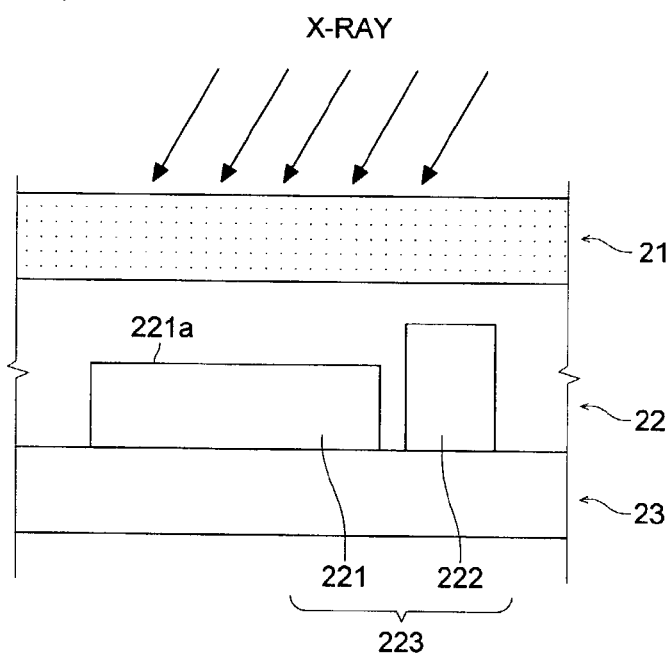
FIG. 2(b) is a cross-section illustrating the structure of the FPD including the TFT in one imaging element.

As shown in FIG. 2(a), FPD 2 is composed of X-ray/fluorescence conversion layer 21 which detects the X-rays which have penetrated subject S and converts the X-rays as fluorescence, photo-electric conversion layer 22 which converts the fluorescence to electrical signals, and glass base plate 23 (see FIG. 2(b)) of a predetermined thickness, and FPD 2 is structured so that photo-electric conversion layer 22 and X-ray conversion layer 21 are stacked in the order on glass base plate 23.

X-ray/fluorescence conversion layer 21 is structured in the same way as conventional X-ray/fluorescence conversion layers, for example, and employs crystals of a fluorescent substance used for a screen film (S/F) which, for example, may be arranged in a flat form. This fluorescent substance is one having the nature that the fluorescent substance emits fluorescence proportional to the intensity of the X-rays which have been radiated from X-ray radiating apparatus 1 and have passed through subject S.

Photo-electric conversion layer 22 has a large number of imaging elements 223 which are composed of light receiving sensors (sensor elements) 221 that detect the fluorescence converted from the X-rays and convert them to electric signals, and TFTs (Thin Film Transistor; a switching element) 222 that perform switching of the read-out of electrical signals outputted from light receiving sensors 221, conducted by electric signal read-out device 31, and both TFTs and the light receiving sensors which are arranged as a matrix on glass base 23.

Light receiving sensors 221 and TFTs 222 may be arranged, for example, in line on glass base 23, and are formed, for example, of a semiconductor such as an amorphous silicone. Further, light receiving sensor 221 has an upper surface which is light receiving surface (a surface for receiving fluorescence) 221a, and the height of light receiving surface 221a is less than that of TFT 222 (see FIG. 2(b)).

Incidentally, concerning TFT 222, gate electrode 222g is connected to a selection line (a gate line, not illustrated), and drain electrode 222d connected to a signal line (not illustrated). Further, source electrode 222 is connected to capacitor 224 which stores electrical signals converted by light receiving sensors 221.

Digital conversion section 3 is provided with electrical signal read-out device 31 which has an electrical signal read-out circuit for reading out electrical signals which are outputted from light receiving sensors 221 and stored in capacitor 224, log amplifier 32 which performs amplification and log-conversion of the above-mentioned electrical signals, and A/D converter 33 which converts electric signals, that have been amplified and log-converted, to digital image data.

When pulses are outputted from gate drivers (not illustrated), and TFTs 222 connected to each selection line are activated, electric signal read-out device 31 selects the signal lines in turn, and reads out, from each imaging element 223, all of the electric signals outputted to the signal lines to which each imaging element 223 is connected.

Computer 4 is provided with memory device 41 such as, for example, a hard disk, to store the digital image data, and further, computer 4 is provided with a CPU (Central Processing Unit), ROM (Read Only Memory), RAM (Random Access Memory) and an interface, with which it controls each of the structuring elements of X-ray imaging apparatus 100.

Specifically, when slanting radiography (described later) is performed, computer 4 functions as a correcting means to correct digital image data which form the X-ray image, in accordance with the radiating angle data based on the radiating angle.

Incidentally, the radiating angle data are the data about the intensity of X-rays which is attenuated from the intensity of X-rays whose radiating angle is a right angle, at each radiating angle at which X-rays are radiated to FPD 2 from the X-ray radiating apparatus, and the radiating angle data are calculated in advance and stored in the ROM. Further, slanting radiography means radiography in which the radiating angle of the X-rays is set to be less than a right angle to the front surface of FPD 2.

Next, control and operation of slanting radiography for X-ray imaging apparatus 100 will be described.

Initially, the radiographing region of subject S is arranged in front of FPD 2. Next, X-ray radiating apparatus 1 is arranged so that X-rays are optimally radiated into the radiographing region. Then computer 4 calculates the radiating angle of the X-rays which are radiated onto FPD 2 from where X-ray radiating apparatus 1 is located. After that, when X-rays are radiated from X-ray radiating apparatus 1, the X-rays which penetrated subject S are converted to fluorescence by X-ray/fluorescence conversion layer 21, the fluorescence is converted to electrical signals by light receiving sensors 221, and TFT 222 is regulated so that electrical signal read-out device 31 reads out the electrical signals from each of imaging elements 223.

Next, the read-out electrical signals are amplified and log-converted by log-amplifier 32, and converted to digital image data by A/D converter 33. Subsequently, the digital image data are sent to computer 4.

Computer 4 determines whether the calculated radiating angle is or is not a right angle. When the radiating angle is determined to be a right angle, the digital image data are stored in memory device 41 without correction. On the other hand, when the radiating angle is judged not to be a right angle, the digital image data are corrected based on the radiating angle data, and the corrected digital image data are stored in memory device 41.

Incidentally, the stored digital image data are used for diagnosis, the necessary image processing suitable for diagnosis is effected using the stored digital image data, the stored digital image data are displayed on CRT display 5, or the stored digital image data are printed by image print device 6.

As mentioned above, X-ray imaging apparatus 100 of the present embodiment corrects the digital image data which are outputted from light receiving sensor 221, after which A/D conversion is performed for the digital image data by A/D converter 33 based on the radiating angle of the X-rays, and thereby, it is possible to correct the digital image data based on the radiating angle and obtain an X-ray image of high resolution, even when the amount of fluorescence, which light receiving sensors 221 receive, decreases.

Specifically, X-ray imaging apparatus 100 of the present embodiment performs correction of the digital image data after A/D conversion is completed, however, there is no limit to this embodiment, that is, timing for the correction is not restricted, as long as correction is performed, before the digital image is converted to an X-ray image and is used for diagnosis. For example, correction of the digital image data can be performed after the digital image data are stored in memory device 41, or correction of the digital image data can be performed just before the digital image data stored are outputted on CRT display 5 or image printing device 6. Further, it is possible to perform correction of the electrical signals before A/D conversion to the digital image data.

Variation 1

The X-ray imaging apparatus of variation 1 is provided with florescence reflecting film (reflecting plate) 225 which reflects at least a part of the florescence converted from the X-rays which enter FPD 302 slantwise. Incidentally, FIG. 3 illustrates a sectional structure of FPD 302 including TFT 222 in one imaging element 323.

Fluorescence reflecting film 225 of a predetermined thickness is provided in each imaging element 323 that composes FPD 302, and is arranged so that the reflecting surface, which reflects the fluorescence, faces light receiving sensor 221 and surrounds the periphery of TFT 222.

Fluorescence reflecting film 225 is composed in such a way, for example, that after the periphery of TFT 222 is covered with an insulating member, vacuum evaporation of a metal which reflects the fluorescence is conducted on the surface. Further, fluorescence reflecting film 225 is higher than light receiving surface 221a, and is arranged to be lower than the lowest face of X-ray conversion layer 21.

Figure 3:
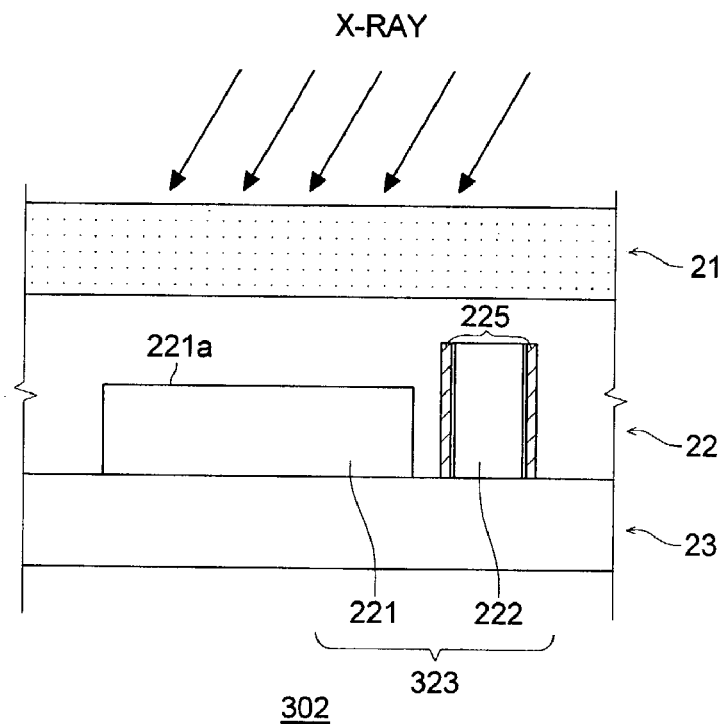
FIG. 3 is a cross-section illustrating the structure of the FPD including TFT in one imaging element, housed in the X-ray imaging apparatus of variation 1.

Incidentally, in FIG. 3, only fluorescence reflecting films 225 and 225 arranged to sandwich TFT 222 from a left and right sides are illustrated in FIG. 3.

In the X-ray imaging apparatus of variation 1, FPD 302 is provided with fluorescence reflecting film 225, which reflects at least a part of the fluorescence converted from the slanted X-rays incident to FPD 302, when the slanting radiography is performed.

Thus, due to fluorescence reflecting film 225, it is possible to reflect the fluorescence, which cannot be detected directly by light receiving sensor 221 because of an obstacle such as TFT 222, among all fluorescence converted from the incident X-rays. Accordingly, there is no reduction of the amount of fluorescence which will be received by light receiving sensor 221, and any deterioration of the sensitivity caused by the slanting radiography is prevented so that the X-ray image with high resolution is obtained.

Incidentally, in variation 1, fluorescence reflecting film 225 is arranged to surround TFT 222, however, the invention is not limited to this, and fluorescence reflecting film 225 can be arranged at any location where at least a part of the fluorescence, which is converted from the X-rays that entered FPD302, can be reflected to the light receiving sensor 221. For example, it is possible to make the composition in which the top of TFT 222 is also covered with the fluorescence reflecting film. Further, a fluorescence reflecting plate can be adjusted instead of fluorescence reflecting film 225, before and behind and left and right of light receiving sensor 221 in FIG. 3.

Variation 2

Figure 4:
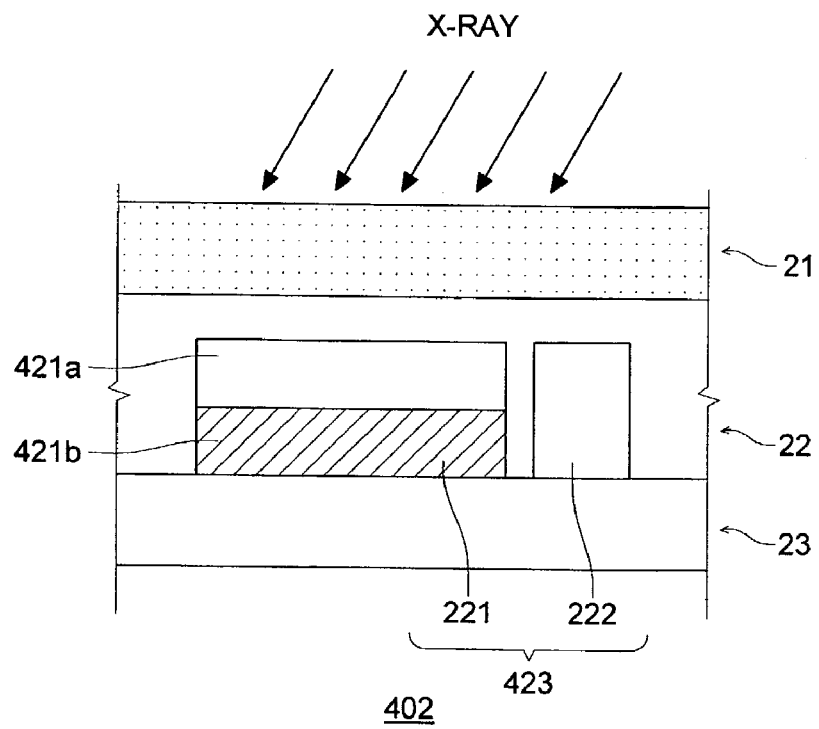
FIG. 4 is a cross-section illustrating the structure of the FPD including TFT in one imaging element, housed in the X-ray imaging apparatus of variation 2.

As shown in FIG. 4, the X-ray imaging apparatus of variation 2 is provided with FPD 402 in which the top surface of light receiving sensor 421a of light receiving sensor 421 is nearly equal to or higher than that of TFT 222. Incidentally, FIG. 4 illustrates a sectional structure of FPD 402 including TFT 222 of one imaging element 423.

Light receiving sensor 421 is provided with base section 421b on its lower section, and thus light receiving section 421a is higher. Incidentally, it is possible to house wiring, which connects light receiving sensor 421 with TFT 222, in base section 421b.

In the X-ray imaging apparatus of variation 2, since the top surface of light receiving sensor 421a of light receiving sensor 421 is nearly equal to or higher than that of TFT 222, for the slanting radiography, light receiving sensor 421 can exactly detect the fluorescence which is converted from the incident X-rays, without being blocked by TFT 222. Accordingly, the amount of the fluorescence which will be received by light receiving sensor 421 is not reduced so that deterioration of sensitivity caused by slanting radiography is prevented, and it is possible to obtain X-ray images of high resolution.

The X-ray imaging apparatus of the present embodiment is provided with X-ray/fluorescence conversion layer 21 and light receiving sensor 221 (421) which detects the fluorescence converted from the X-rays, however, the invention is not limited to this, for example, it may be structured without having X-ray/fluorescence conversion layer 21, and instead of light receiving sensor 221 (421), it is possible to use an X-ray detecting section (sensor element) which directly detects the X-rays. In this case, even when the amount of X-rays which will be received by the X-ray detecting section is reduced, the electrical signals outputted from the X-ray detector can be corrected in accordance with the angle of radiation, and thereby, X-ray images with high resolution can be obtained.

Further, in the X-ray imaging apparatus having the above mentioned structure, it is possible to arrange an X-ray reflecting plate which reflects X-rays onto the X-ray detecting section, still further, the height of the X-ray detecting surface of the X-ray detecting section can be positioned to be equal to or higher than that of the TFT in FPD. Under the above-mentioned structure, among all incident X-rays, these X-rays, which cannot be detected directly by the X-ray detector due to an obstacle such as TFT, can be reflected to the X-ray detecting section by the X-ray reflecting plate, or the incident X-rays can be detected precisely by the X-ray detecting section without being obstructed by TFT, and thereby, the amount of the X-rays which will be detected by the X-ray detecting section is not reduced so that any deterioration of the sensitivity caused by the slanting radiography is prevented, and it is possible to obtain X-ray images with high resolution.

According to the invention described in Structure (1), when radiography is performed with the radiating angle of the radiation to the radiographing region, that is, slanted from a right angle to the front surface of the flat panel detector, there is provided a correcting device that corrects the signal showing the intensity of the radiation outputted from the sensor element, in accordance with the angle of the radiation, and thereby, radiation images with high resolution can be obtained, because the signal showing the intensity of the radiation outputted from the sensor element can be corrected based on the angle of radiation, even though the amount of radiation received by the sensor element or the amount of fluorescence converted from the radiation is decreased.

According to the invention described in Structure (2), the flat panel detector is provided with reflecting plates which reflect at least one part of the radiation slanting to the flat panel detector, or at least one part of fluorescence converted from the radiation, and thereby, among the incident radiations or the fluorescence converted from the radiation, it is possible to reflect the incident radiation or the fluorescence converted from the radiation, which is not detected directly by a sensor element due to an obstacle such as the switching element, to the sensor element by the reflecting plate. Accordingly, there is no decrease of the amount of radiation or the amount of fluorescence which will be received by the sensor element, and thereby, deterioration of sensitivity caused by the slanting radiograph is prevented so that the radiograph images having high resolution can be obtained.

According to the invention described in Structure (3), since, for slanting radiography, the height of the surface of the sensor element to which the radiation or the fluorescence is incident, is nearly equal to or higher than that of the switching element in the flat panel detector, it is possible to assuredly detect the incident radiation or the fluorescence converted from the radiation by the sensor element, without obstruction caused by the switching element. Accordingly, there is no decrease of the amount of radiation or the amount of fluorescence received by the sensor, and deterioration of sensitivity caused by slanting radiography is prevented so that radiograph images having high resolution can be obtained.

According to the invention described in Structure 4, it is possible to obtain the same effect as that of the invention described in Structure 1.

What is claimed is:

1. A radiation imaging apparatus, comprising:
   a radiation or fluorescence detecting device on which a plurality of imaging elements are arranged in a form of a plane, comprising:
   a sensor element, arranged on the imaging element, to detect radiation or fluorescence converted from the radiation which have penetrated a subject, and to form radiation intensity signals,
   a switching element, arranged on the imaging element, to perform switching of read-out of the radiation intensity signals outputted from the sensor elements; and
   a reflection plate, arranged around the switching element, to reflect slanted radiation or fluorescence converted from the radiation, onto the sensor element.

* * * * *